United States Patent

Zhou et al.

[11] Patent Number: 6,080,387
[45] Date of Patent: Jun. 27, 2000

[54] AEROSOL ANTIMICROBIAL COMPOSITIONS

[75] Inventors: Boli Zhou, Antioch; Maria G. Ochomogo, Danville; Elias A. Shaheen, Walnut Creek, all of Calif.

[73] Assignee: The Clorox Company, Oakland, Calif.

[21] Appl. No.: 09/116,190

[22] Filed: Jul. 15, 1998

[51] Int. Cl.[7] ............................. A61K 9/12; A61K 31/79
[52] U.S. Cl. ................. 424/45; 424/78.31; 424/78.32; 424/78.33; 424/78.35; 424/78.36
[58] Field of Search ........................... 424/45, 486, 405, 424/78.31, 78.32, 78.33, 78.35, 78.36

[56] References Cited

U.S. PATENT DOCUMENTS

| | | | |
|---|---|---|---|
| 2,746,928 | 5/1956 | Darragh | 252/106 |
| 3,093,591 | 6/1963 | Freese | 252/106 |
| 3,344,018 | 9/1967 | Shibe | 167/22 |
| 3,471,423 | 10/1969 | Elmer | 260/22 |
| 3,560,390 | 2/1971 | Gaines | 252/107 |
| 3,719,711 | 3/1973 | Temple | 260/567.6 P |
| 4,272,395 | 6/1981 | Wright | 252/106 |
| 4,476,251 | 10/1984 | Cianciolo | 521/110 |
| 4,576,729 | 3/1986 | Paszek et al. | 252/106 |
| 4,759,867 | 7/1988 | Choy | 252/143 |
| 4,783,340 | 11/1988 | McDonell et al. | 427/2 |
| 4,883,828 | 11/1989 | Oakes | 523/122 |
| 4,908,381 | 3/1990 | Greenwald | 514/460 |
| 4,935,232 | 6/1990 | McIntosh | 424/78 |
| 5,028,619 | 7/1991 | Rei | 514/372 |
| 5,061,485 | 10/1991 | Oakes | 424/81 |
| 5,108,740 | 4/1992 | Greenwald | 424/78.32 |
| 5,399,343 | 3/1995 | Smith et al. | 424/61 |
| 5,482,989 | 1/1996 | Koskiniemi | 524/404 |

FOREIGN PATENT DOCUMENTS

| | | |
|---|---|---|
| 311 344 | 4/1989 | European Pat. Off. . |
| 98/30665 | 7/1998 | WIPO ............ C11D 3/00 |
| WO 98/40 452 | 9/1998 | WIPO . |

OTHER PUBLICATIONS

Zeneca Biocides: A New Durable Antiodor Finish for Cotton Textiles.
Patent Abs. of Japan: vol. 14, No. 535 (Nov. 26, 1990).
Patent Abs. JP63301251 (Aug. 12, 1988).

*Primary Examiner*—Thurman K. Page
*Assistant Examiner*—R. Bawa
*Attorney, Agent, or Firm*—Joel J. Hayashida

[57] ABSTRACT

An aerosol antimicrobial composition is provided with the following ingredients: a) an anionic polymer or prepolymer; (b) a quaternary ammonium compound, the components (a) and (b) combining to form an antimicrobially effective complex; (c) at least one water-soluble or dispersible organic solvent having a vapor pressure of at least 0.001 mm Hg at 25° C., said at least one organic solvent present in a solubilizing—or dispersion—effective amount; (d) an effective amount of a propellant; and (e) the remainder, water. Further is provided a novel method of decontaminating a surface fouled with microorganisms and a dispenser for said aerosol composition. The novel composition advantageously has both disinfectancy (contact efficacy) and residual antimicrobial efficacy.

14 Claims, No Drawings

AEROSOL ANTIMICROBIAL COMPOSITIONS

FIELD OF THE INVENTION

The present invention relates generally to dispensable antimicrobial compositions, and more particularly to an aerosol composition which has both disinfectancy (contact efficacy) and residual antimicrobial efficacy.

BACKGROUND OF THE INVENTION

In the seemingly perpetual battle against infection by pathogenic microorganisms, a recent, alarming trend has been observed. Antibiotic medications and treatments long thought to have conquered, if not arrested, the invasive infection of humans by such pathogens (generally, prokaryotic organisms, such as bacteria), have recently begun to fail or lose effectiveness at stopping such infections. Terrifying, and seemingly increasingly frequent, news stories of either fatal or serious infection by such bacteria as the common intestinal inhabitant *Escherichia coli* 0.157 (especially affecting small children and those with a lesser, or challenged immune system), and by certain species of Staphylococcus sp. (colorfully, but somewhat inaccurately dubbed in news accounts as "flesh eating bacteria") have led to the conclusion that prevention, by decontamination of surfaces touched by humans, may indeed be a wiser remedy than cure by antibiotics. So, the search for appropriate antimicrobial treatments of surfaces is spurred by this new challenge by these old enemies of the human population.

The use of quaternary ammonium compounds as antimicrobial agents is well known in the art. See U.S. Pat. Nos. 2,746,928, 3,344,018, 3,719,711, and JP 01/046081. For instance, quaternary ammonium compounds have been incorporated into polymer and liquid compositions to protect the compositions themselves from microbial attack (i.e., used as preservatives). See U.S. Pat. Nos. 3,471,423, 5,028,619 and 5,399,343. Furthermore, quaternary ammonium compounds have also been employed as an additive in a variety of household products including detergents. See U.S. Pat. Nos. 3,093,591, 3,560,390, 4,272,395 and 4,576,729.

An effort to remedy the issues faced by prior antimicrobial compositions was posed in the commonly owned U.S. patent application Ser. No. 08/833,276, filed Apr. 4, 1997, of Boli Zhou et al., the disclosure of which is incorporated herein by reference. This Patent Application contemplated the formation of a novel mixed anionic/cationic polymer having residual antimicrobial efficacy. However, the application did not disclose, suggest or teach that an aerosol composition containing a mixture of an anionic polymer and a quaternary ammonium compound has both disinfectancy (contact efficacy) and residual antimicrobial efficacy. There are also various compositions, especially hard surface cleaners, which have been delivered as aerosols but which do not contain the inventive mixture of an anionic polymer and a quaternary ammonium compound having both disinfectancy (contact efficacy) and residual antimicrobial efficacy.

SUMMARY OF THE INVENTION

The invention is an antimicrobial dispensable composition comprising:

(a) an anionic polymer or prepolymer;

(b) a quaternary ammonium compound, the components (a) and (b) combining to form an antimicrobially effective complex;

(c) at least one water-soluble or dispersible organic solvent having a vapor pressure of at least 0.001 mm Hg at 25° C., said at least one organic solvent present in a solubilizing—or dispersion—effective amount;

(d) an effective amount of a propellant; and (e) the remainder, water.

In one aspect, the invention is directed to a dispensable composition for treating surfaces which contain microorganisms.

In another aspect, the invention is directed to a method for decontaminating a surface containing microorganisms by contacting the surface with the dispensable composition.

In a further aspect, the invention is directed to a device, for dispensing a composition for treating a surface containing microorganisms, which includes, a pressurized closed container containing the above antimicrobial composition and nozzle means for releasing said composition towards a contaminated surface.

It is therefore an object and an advantage of the present invention to provide antimicrobial composition which has both disinfectancy (contact efficacy) and residual antimicrobial efficacy.

It is another object and another advantage of the present invention to provide a convenient and easy to use product which has prolonged residual efficacy in a single treatment of surfaces, which thus reduces labor, time, effort and cost to treat such surfaces.

It is a further object and advantage of the present invention to provide a method for decontaminating a surface containing microorganisms, or which can be potentially contaminated thereafter.

It is a still further object and advantage of this invention to provide a dispensable antimicrobial composition which contacts a surface and forms thereon a film or residue which has prolonged antimicrobial efficacy.

It is yet another object and advantage of this invention to provide a dispensable antimicrobial composition which has up to 99.9% residual efficacy in a 24 hour period.

It is a final object and advantage of this invention to provide a dispensable antimicrobial composition which outperforms commercially available products which claim to have antimicrobial efficacy.

DETAILED DESCRIPTION OF THE INVENTION

The invention provides an aerosol formulation comprising a novel antimicrobial composition for treating one or more surfaces containing microorganisms. These surfaces include those which are typically contacted by human touch: bathroom surfaces, such as a bath tub, sink, commode, toilet, or shower stall, which may have glass doors, and include vertical wall surfaces typically made of tile, glass, or composite materials; kitchen surfaces, such as countertops, stove tops, sinks, table tops, chairs; and generally, any other surface, whether hard or soft, such as furniture, window ledges, window frames and other edges, door knobs, handles, tools, appliances, utility devices (such as telephone handsets and portable telephones), implements (such as pens, mechanical pencils and the like), wrist watches, clothing (such as stockings), shoes, outer garments, and other common and uncommon surfaces. Each of these types of surfaces can act to harbor microorganisms, including bacteria, fungi, molds, mildew and viruses. Thus, each such surface can communicate a potential infectious vector to the unwitting person (or, in the case of cross-species infection, household pets) unless treated with an appropriate antimicrobial composition. The inventive antimicrobial composition is intended to so treat and decontaminate such surfaces, and others, by aerosol application of a metered discrete amount of the composition via a dispenser onto the surface to be treated. The antimicrobial composition is generally merely applied as an aerosol composition to the surface in order to effect antimicrobial efficacy. The surface can additionally be spread or wiped, but this would then remove the composition and may lessen the efficacy thereof.

The antimicrobial composition is formulated with ingredients which themselves are found often in cleaners, such as hard surface and fabric cleaners. Thus, an additional benefit of the composition is that it can also act as a cleaner and soil remover. It is preferred that this benefit be achieved without detriment to its primary advantage as an antimicrobial composition.

The aerosol formulation comprises an antimicrobial composition that is mixed with a propellant. The composition has the following ingredients:

(a) an anionic polymer or prepolymer;

(b) a quaternary ammonium compound, the components (a) and (b) combining to form an antimicrobially effective complex;

(c) at least one water-soluble or dispersible organic solvent having a vapor pressure of at least 0.001 mm Hg at 25° C., said at least one organic solvent present in a solubilizing—or dispersion—effective amount;

(d) an effective amount of a propellant; and (e) the remainder, water.

Additional adjuncts in small amounts such as buffers, fragrances, dyes and the like can be included to provide desirable attributes of such adjuncts.

In the application, effective amounts are generally those amounts listed as the ranges or levels of ingredients in the descriptions which follow hereto. Unless otherwise stated, amounts listed in percentage ("%'s") are in weight percent (based on 100% active) of the cleaning composition.

1. Anionic Polymer or Prepolymer

The anionic polymer or prepolymer (generally, component) generally has an acid number greater than 10. It is an essential part of the invention since it combines with the quaternary ammonium compound in a mechanism which, as yet, is not completely understood, and may or may not involve an ionic bonding, or pairing, mechanism. The anionic component is usually a polymer having an average molecular weight of about 100 to about 2,000,000 daltons, with an acid number preferably greater than about 10. As used herein, "acid number" retains its conventional meaning and is determined by the number of milligrams of potassium hydroxide required for the neutralization of the corresponding acids of the anionic groups present in one gram of the polymer.

In the antimicrobial composition, the anionic component may or may not be partially or completely neutralized by the quaternary ammonium compound to form a polymer complex. The actual manner of combining of the two key components of the inventive antimicrobial compositions has not been fully determined at this time. Thus, instead of ionic bonding, as in the classic sense of anionic and cationic materials forming an ion pair (See *Cationic Surfactants, Physical Chemistry,* in: Surfactant Science Series Vol. 37, p. 93 (Marcel Dekker, 1983)), when the liquid, dispensable compositions of this invention are delivered from the dispenser to a surface, physical association may actually be taking place, such as occlusion, where the quaternary ammonium compound is evenly dispersed in the resulting polymer matrix or film. It is also speculated that, in the dispenser, the components may also form another state in which ion pairing does take place. However, all of the foregoing is by way of non-binding theory.

The antimicrobial composition is preferably prepared by mixing effective amounts of the anionic component and the quaternary ammonium compound in water with agitation. A water miscible solvent and/or dispersing/emulsifying/wetting agent is preferably added before the two main components are mixed together. The "dispersing/emulsifying/wetting agent" comprises any suitable agent which will cause the admixture of anionic component and the quaternary ammonium compound to be stably distributed substantially homogeneously in the liquid composition. Depending on the particular anionic components and quaternary ammonium compounds used to make the composition, the presence of cross-linkers, stabilizers and other variables, the antimicrobial compositions of the invention may exist as emulsions, suspensions, dispersions, solutions, or possibly, as other forms of liquids, such as microemulsions and liquid crystals.

The anionic component, which can be a polymer or prepolymer, is preferably derived from monomers having anionic groups attached thereto. Preferably, the polymer has an average molecular weight of about 200 to 2,000,000, more preferably, about 2,000 to 1,000,000, and most preferably, about 5,000 to 150,000 daltons, with an acid number greater than about 10 and preferably from about 60 to 700.

Preferred anionic polymers are selected from the group consisting of: (1) a homopolymer that is selected from the group consisting of vinyl sulfonates, acrylates, methacrylates, styrene sulfonates, maleates, vinyl sulfates and mixtures thereof; (2) a copolymer that is derived from (i) one or more anionic monomers selected from the group consisting of vinyl sulfonates, acrylates, methacrylates, styrene sulfonates, maleates, vinyl sulfates; and (ii) one or more nonionic monomers selected from vinyl esters, vinyl alcohols, vinyl ethers, acrylamides, methacrylamides, alkyl or aryl acrylates, alkyl or aryl methacrylates, alkyl or aryl maleates, acrylonitriles, vinyl pyrrolidones, alkenes, such as, for example, styrene, ethylene and propylene, multifunctional acids, polyols, multifunctional amines, multifunctional isocyanates and multifunctional epoxy compounds; and (3) methylcarboxycellulose.

As is apparent, copolymers may include nonionic monomers. A preferred copolymer comprising nonionic and anionic monomers is formed from acrylic acid esters, such as methacrylate or acrylate. The anionic polymers can be in their salt, acid, or partially protonated forms.

The solubility/dispersability of the polymer will depend, in part, on its molecular weight, acid number, and the solvent and/or wetting/dispering/emulsifying agent involved. Optionally, the anionic polymer or component may be cross-linked with common cross-linkers such as, for example, carbodiimide, aziridine, polyols, glyoxal, epoxy compounds, transition metal ions, and ionene polymers (See also the cross-linking agents described in U.S. patent application Ser. No. 09/023,093, filed Feb. 13, 1998, of Shaheen et al., incorporated herein by reference) to reduce solubility. Typically, in formulating a liquid, dispensable antimicrobial composition, the anionic polymer is present in an amount of about 0.01 to 15%, more preferably about 0.1 to 10%, and most preferably, about 0.5 to 5%, by weight of the composition. Important examples of the preferred anionic polymers include the acrylate copolymers produced by B.F. Goodrich under the trademark Carboset. Especially preferred is Carboset Ga. 2123, which appears to be an acrylic acid/acrylate ester copolymer. There further appears to be a preferential ratio of the anionic component to the quaternary ammonium compound. This ratio may be from about 1:100 to about 100:1, more preferably about 1:10 to about 10:1, and most preferably, about 5:1 to about 1:5. In balancing the ratio of anionic component to quaternary ammonium compound, one must keep in mind the desirable characteristics in the dispenser (i.e., "can stability") versus that of the dispensed liquid versus that of the cured or dried film/residue (when the liquids/solvents volatilize or "flash off"). The more anionic polymer, the smoother, glassier appearing of the resulting film, and the more water soluble. The more quaternary ammonium compound, the less water soluble the resulting film, but, aesthetics of the film appear to become less pleasing, however, such less attractive forms are still part of the invention. The most preferred range of 5:1 to 1:5 appears to result in an aesthetically pleasing film which has excellent residual antimicrobial efficacy, as well as disinfectancy. This also seems to imply that, in the cured film/residue, there may actually not be complete ion pairing between the quaternary ammonium compound and the anionic sites in the anionic polymer, since the quaternary ammonium active sites are available for residual microbial kill, although there is clearly an interaction between the two components. Again, the mechanism of the film/residue is not completely understood, so these latter observations are made by way of non-binding theory. Further, it is preferred to obtain a transparent to translucent, smooth, homogeneous, tack-free film. So, other additives can be added to improve the film's characteristics, such as the use of various water soluble polymers, and by neutralizing some of the acid groups of the anionic polymers by various buffers, such as alkali metal ($Na^+$, $K^+$) and ammonium buffers, although organic buffers, such as alkanolamines may be used. Additionally, some wetting/dispersing/emulsifying agents as described below in 4. help to enable the formation of effective films or residues, by placing the ingredients into dispersion. By "effective" is meant that the films achieve consistent residual efficacy throughout the film.

2. Quaternary Ammonium Compound

A critical second component of the invention is a quaternary ammonium compound, or surfactant. These types of surfactants are typically used in bathroom cleaners because they are generally considered "broad spectrum" antimicrobial compounds, having efficacy against both gram positive (e.g., Staphylococcus sp.) and gram negative (e.g., Escherichia coli or Klebsiella sp.) microorganisms. Thus, the quaternary ammonium surfactant, or compounds, are incorporated for bacteriostatic/disinfectant purposes and should be present in amounts effective for such purposes.

The quaternary ammonium compounds are selected from mono-long-chain, tri-short-chain, tetraalkyl ammonium compounds, di-long-chain, di-short-chain tetraalkyl ammonium compounds, trialkyl, mono-benzyl ammonium compounds, and mixtures thereof. By "long" chain is meant about $C_{6-30}$ alkyl. By "short" chain is meant about $C_{1-5}$ alkyl, preferably $C_{1-3}$. Suitable counterions for such quaternary ammonium compounds include halides (chlorides, bromides, iodides), hydroxides, saccharinates, carbonates, phosphates, phosphonates, sulfates, bisulfates, alkylsulfates, carboxylates, and other negatively charged counterions. Preferred materials include the BTC 885—which comprises a mixture of $C_{12-16}$ alkyl dimethylbenzyl ammonium chloride, $C_8/C_{10}$ alkyl dimethyl ammonium chloride, di-$C_8$ alkyl dimethyl ammonium chloride, and di-$C_{10}$ alkyl dimethyl ammonium chloride—and 2125 series from Stepan, which comprises di-$C_{24}$-dialkyl ammonium chloride, and the Barquat and Bardac series, such as Bardac MB 2050, from Lonza Chemical. Most preferred appears to be a mixed quaternary ammonium surfactant in which there is a combination of di-long-chain, di-short-chain tetraalkyl ammonium compounds, and trialkyl, mono-benzyl ammonium compounds. These particularly preferred quaternary ammonium surfactants form both smooth films with the anionic polymers listed above, but also are the most effective at broad spectrum contact and residual antimicrobial efficacy (both gram negative and gram positive microorganisms), antifungal and antiviral efficacy. Typical amounts of the quaternary ammonium compound range from preferably about 0.01–5%, more preferably about 0.01–2%.

3. Solvents

The solvent is a water soluble or dispersible organic solvent having a vapor pressure of at least 0.001 mm Hg at 25° C. It is preferably selected from $C_{1-6}$ alkanols, $C_{1-6}$ diols, $C_{1-6}$ alkyl ethers of alkylene glycols and polyalkylene glycols, and mixtures thereof. The alkanol can be selected from methanol, ethanol, n-propanol, "isopropanol," the various positional isomers of butanol, pentanol, and hexanol, and mixtures of the foregoing. It may also be possible to utilize in addition to, or in place of, said alkanols, the diols such as methylene, ethylene, propylene and butylene glycols, and mixtures thereof, and including polyalkylene glycols.

It is preferred to use a $C_{1-6}$ alkanol solvent in this invention. The preferred alkanol is ethanol, which advantageously acts as both a solvent, to maintain the ingredients in the liquid composition in dispersion, as well as a disinfectant. If mixtures of solvents are used, the amounts and ratios of such solvents used are important to determine the optimum performances of the inventive composition. It is preferred to have the total amount of solvent to at least 20%, more preferably least 30%, and most preferably, at least 50%, of the composition. A preferred range is about 20–99.9%. These amounts of solvents are generally referred to as dispersion effective or solubilizing effective amounts, since the other components, such as surfactants, are materials which are assisted into solution by the solvents. As in the case of ethanol, the solvent can also have disinfectancy capacity itself. Finally, the solvent is also important as a cleaning materials itself, helping to loosen and solubilize certain soils for easy removal from the surface treated.

4. Wetting/Emulsifying/Dispersing Agent

The wetting/emulsifying/dispersing agent may be preferably a surfactant (preferably, anionic, cationic nonionic, amphoteric, or zwitterionic surfactant; but the quaternary ammonium surfactant of 2., above, is not considered as one of the wetting agents herein), or possibly, a hydrotrope (which is also treated below, in 5.). The surfactant may be an nonionic, amphoteric or zwitterionic surfactant, or mixtures thereof. The following is a nonlimiting description of surfactants which might be employed in the present invention. The description is intended to exemplify that a wide variety of surfactants can be used according to the present invention.

a. Anionic, Nonionic, Amphoteric and Zwitterionic Surfactants

The anionic surfactants may include a negatively charged water solubilizing group.

The nonionic surfactants may be selected from modified polysiloxanes, alkoxylated alcohols, alkoxylated phenol ethers, glycosides, and the like. Trialkyl amine oxides, and other surfactants often referred to as "semi-polar" nonionics, may also be employed.

Most preferred are modified polysiloxanes. The modified polysiloxane can be an alkoxylated dimethylsiloxane, such as those available from Byk Chemie, such as BYK-345.

The alkoxylated alcohols may include, for example, ethoxylated, and ethoxylated and propoxylated $C_{6-16}$ alcohols, with about 2–10 moles of ethylene oxide, or 1–10 and 1–10 moles of ethylene and propylene oxide per mole of alcohol, respectively. Exemplary surfactants are available from Shell Chemical under the trademarks Neodol and Alfonic, and from Huntsman Chemicals under the trademark Surfonic (e.g., Surfonic L12-6, a $C_{10-12}$ ethoxylated alcohol with 6 moles of ethylene oxide, and Surfonic L12-8, a $C_{10-12}$ ethoxylated alcohol with 8 moles of ethylene oxide).

The alkoxylated phenol ethers may include, for example, octyl- and nonylphenol ethers, with varying degrees of alkoxylation, such as 1–10 moles of ethylene oxide per mole of phenol. The alkyl group may vary, for example, from $C_{6-16}$, with octyl- and nonyl chain lengths being readily available. Various suitable products are available from Rohm & Haas under the trademark Triton, such as Triton N-57, N-101, N-111, X-45, X-100, X-102, from Mazer Chemicals under the trademark Macol, from GAF Corporation under the trademark Igepal, and from Huntsman under the trademark Surfonic.

The glycosides, particularly the alkyl polyglycosides, may also be used as a surfactant for purposes of the aerosol formulation of the present invention. These glycosides include those of the formula:

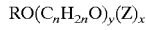

wherein R is a hydrophobic group (e.g., alkyl, aryl, alkylaryl etc., including branched or unbranched, saturated and unsaturated, and hydroxylated or alkoxylated members of the foregoing, among other possibilities) containing from about 6 to about 30 carbon atoms, preferably from about 8 to about 15 carbon atoms, and more preferably from about 9 to about 13 carbon atoms; n is a number from 2 to about 4, preferably 2 (thereby giving corresponding units such as ethylene, propylene and butylene oxide); y is a number having an average value of from 0 to about 12, preferably 0; Z is a moiety derived from a reducing saccharide containing 5 or 6 carbon atoms (e.g., a glucose, fructose, mannose, galactose, talose, gulose, allose, altrose, idose, arabinose, xylose, lyxose, or ribose unit, etc., but most preferably a glucose unit); and x is a number having an average value of from 1 to about 10, preferably from 1 to about 5, and more preferably from 1 to about 3.

It would be apparent that a number of variations with respect to the makeup of the glycosides are possible. For example, mixtures of saccharide moieties (Z) may be incorporated into polyglycosides. Also, the hydrophobic group (R) can be attached at the 2-, 3-, or 4-positions of a saccharide moiety rather than at the 1-position (thus giving, for example, a glucosyl as opposed to a glucoside). In addition, normally free hydroxyl groups of the saccharide moiety may be alkoxylated or polyalkoxylated. Further, the $(C_nH_{2n}O)_y$ group may include ethylene oxide and propylene oxide in random or block combinations, among a number of other possible variations.

An exemplary glycoside surfactant is APG 325n, which is manufactured by the Henkel Corporation. APG 325n is a nonionic alkyl polyglycoside in which R is a mixture of $C_8$, $C_9$, $C_{10}$ and $C_{11}$ chains in a weight ratio respectively of 20:40:40 (equivalent to an average of $C_{10.2}$), with x of 1.6, and an HLB of 13.1.

Compositions containing other surfactants, such as some amine oxides, may be less compatible with the tin-plated steel can environment (or even with steel cans that are lined with, e.g., an epoxy phenolic coating). Tin-plated steel cans are desirable as containers for aerosol compositions because they are more readily available and are less expensive than aluminum or specially lined steel cans.

The amine oxides, referred to as mono-long chain, di-short chain, trialkyl amine oxides, have the general configuration:

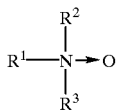

wherein $R^1$ is $C_{6-24}$ alkyl, and $R^2$ and $R^3$ are both $C_{1-4}$ alkyl, or $C_{1-4}$ hydroxyalkyl, although $R^2$ and $R^3$ do not have to be equal. These amine oxides can also be ethoxylated or propoxylated. The preferred amine oxide is lauryl amine oxide. The commercial sources for such amine oxides are Barlox 10, 12, 14 and 16 from Lonza Chemical Company, Varox by Witco and Ammonyx by Stepan Company.

A further semi-polar nonionic surfactant is alkylamidoalkylenedialkylamine oxide. Its structure is shown below:

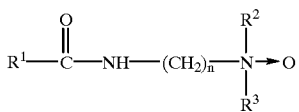

wherein $R^1$ is $C_{5-20}$ alkyl, $R^2$ and $R^3$ are $C_{1-4}$ alkyl, $R^1$—C—NH—$(CH_2)_n$— or —$(CH_2)_p$—OH, although $R^2$ and $R^3$ do not have to be equal or the same substituent, and n is 1–5, preferably 3, and p is 1–6, preferably 2–3. Additionally, the surfactant could be ethoxylated (1–10 moles of EO/mole) or propoxylated (1–10 moles of PO/mole). This surfactant is available from various sources as a cocoamidopropyldimethyl amine oxide; it is sold by Lonza Chemical Company under the brand name Barlox C. Additional semi-polar surfactants may include phosphine oxides and sulfoxides.

A preferred cationic surfactant is morpholinium ethosulfate, such as Forestall (Atlas) G-271.

The amphoteric surfactant is typically an alkylbetaine, an amidobetaine, or a sulfobetaine. One group of preferred amphoterics are alkylamidoalkyldialkylbetaines. These have the structure:

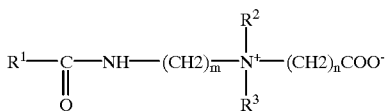

wherein $R^1$ is $C_{6-20}$ alkyl, $R^2$ and $R^3$ are both $C_{1-4}$ alkyl, although $R^2$ and $R^3$ do not have to be equal, and m can be 1–5, preferably 3, and n can be 1–5, preferably 1. These alkylbetaines can also be ethoxylated or propoxylated. The preferred amidobetaine is cocoamidopropyldimethyl betaine, available from Lonza Chemical Co. as Lonzaine CO. Other vendors are Henkel KGaA, which provides Velvetex AB, and Witco Chemical Co., which offers Rewoteric AMB-15, both of which products are cocobetaines.

Potentially suitable zwitterionic surfactants can be found described in Jones, U.S. Pat. No. 4,005,029, at columns 11–15, which are incorporated herein by reference.

The amounts of surfactants present are to be somewhat minimized, for purposes of cost-savings and to generally restrict the dissolved actives which could contribute to leaving behind residues when the aerosol is applied to a surface. However, the amounts added are generally about 0.001–5%, more preferably 0.002–3.00% surfactant. These are generally considered to be dispersion-effective amounts.

5. Water and Miscellaneous

Since the composition is an aqueous composition, water can be, along with the solvent, be a predominant ingredient. The water should be present at a level of less than 70%, more preferably less than about 65%, and most preferably, less than about 50%. Deionized water is preferred.

Small amounts of adjuncts can be added for improving performance, stability or aesthetic qualities of the composition. For example, buffers can be added to maintain a constant pH (which for the invention is between about 5–14, more preferably between about 8–13; formulations containing the tripotassium and/or triammonium salts will naturally be at a lower end of the range as compared to the corresponding tetra salts). These buffers include, for example, NaOH, KOH, $Na_2CO_3$, and $K_2CO_3$ as alkaline buffers, and phosphoric, hydrochloric, sulfuric, and citric acids as acidic buffers, among others. It may be desirable to add chelating agents, such as polycarboxylates (e.g., EDTA and its alkali metal and ammonium salts), aminopolyphosphonates and polyphosphonates, metasilicates and organic amines. Chelating agents may help to potentiate antimicrobial efficacy or have other functional uses.

Further solubilizing materials, such as hydrotropes (e.g., water soluble salts of low molecular weight organic acids such as the sodium or potassium salts of cumene-, toluene-, benzene-, and xylene sulfonic acid), may also be desirable. Adjuncts for cleaning include additional surfactants, such as those described in *Kirk-Othmer, Encyclopedia of Chemical Technology*, 3rd Ed., Volume 22, pp. 332–432 (Marcel-Dekker, 1983), and *McCutcheon's Soaps and Detergents* (N. Amer. 1984), which are incorporated herein by reference. Aesthetic adjuncts include fragrances or perfumes, such as those available from Givaudan, IFF, Quest, Sozio, Firmenich, Dragoco and others, and dyes or colorants which can be solubilized or suspended in the formulation, such as diaminoanthraquinones. Enhancing ingredients, such as nerolidol, may be present to perform in multiple capacities, both aesthetic and functional, the composition (See commonly owned U.S. patent application Ser. No. 09/085,340, of Shaheen et al., filed May 27, 1998, and incorporated herein by reference). Water-insoluble solvents may sometimes be desirable as added grease- or oily soil-cutting agents. These types of solvents include tertiary alcohols, hydrocarbons (e.g., alkanes), pine-oil, d-limonene and other terpenes and terpene derivatives, and benzyl alcohols. Thickeners, such as calcium carbonate, sodium bicarbonate, aluminum oxide, and polymers, such as polyacrylate, starch, xanthan gum, alginates, guar gum, cellulose, and the like, may be desired additives, although care must be taken since the inventive compositions are meant to be relatively thin liquids for effective dispensation from a pressurized canister. The use of some of these thickeners (e.g., $CaCO_3$ or $NaHCO_3$) is to be distinguished from their potential use as builders, generally by particle size or amount used. Additional additives may include further antimicrobial compounds, such as phenols (See, Moseman, U.S. Pat. No. 4,985,945, incorporated herein by reference), pine oil (See Spaulding et al., U.S. Pat. No. 4,867,898, incorporated herein by reference) and liposome-like microemulsions such as mentioned in the paper by T. Hamouda et al., "Microbiocidal Effects of Liposomes-Like Microemulsions on Pathogenic Gram Negative Bacteria," in: Poster Session 251/A Antimicrobial Therapy and Charactertization of Pathogens, American Society of Microbiology 98th Annual Meeting, May 17–21, 1998, p. 152, said paper incorporated herein by reference.

As already noted above, the preferred container for dispensing of the present composition in aerosol form is a tin-plated steel can, but other aerosol packages may be suitable for use. Therefore, it is advantageous to add one or more corrosion inhibitors to prevent or at least reduce the rate of expected corrosion of such a metallic dispenser. Chloride salts, if present, may cause corrosion. Preferred corrosion inhibitors include, for example, sodium nitrite, potassium nitrite, sodium benzoate, potassium benzoate, amine neutralized alkyl acid phosphates and nitroalkanes, amine neutralized alkyl acid phosphates and volatile amines, diethanolamides, amine borates, hydroxylamines, alkanolamines, amine carboxylates, esters, volatile silicones, amines and mixtures thereof. Specific inhibitors include, for example, sodium lauroyl sarcosinate, available from Stepan Company under the trademark Maprosyl 30, sodium meta silicate, sodium or potassium benzoate, triethanolamine, and morpholine. When employed, the corrosion inhibitor preferably comprises about 0.01% to 5% of the aerosol formulation.

6. Propellant

The antimicrobial composition is delivered in the form of an aerosol. The propellant comprises, for example, a hydrocarbon, of from 1 to 10 carbon atoms, such as methane, ethane, n-propane, n-butane, isobutane, n-pentane, isopentane, and mixtures thereof. The propellant may also be selected from halogenated hydrocarbons including, for example, fluorocarbons, chlorocarbons, chlorofluorocarbons, and mixtures thereof. (Besides of concerns about the destruction of the stratosphere's ozone layer, the use of fluorocarbons and chlorofluorocarbons is less preferred.) Examples of other suitable propellants are found in P. A. Sanders *Handbook of Aerosol Technology* (Van Nostrand Reinhold Co.) (1979) 2nd Ed., pgs. 348–353 and 364–367, which are incorporated by reference herein. Further, non-hydrocarbon propellants may be possible, such as carbon dioxide, nitrogen, compressed air, and, possibly, dense or supercritical fluids.

A liquefied gas propellant mixture comprising about 85% isobutane and 15% propane is preferred because it provides sufficient pressure to expel the cleaning composition from the container and provides good control over the nature of the spray upon discharge of the aerosol formulation. Preferably, the propellants comprises about 1% to 50%, more preferably about 2% to 25%, and most preferably about 5% to 15% of the aerosol formulation.

The aerosol formulation is preferably stored in and dispensed from a pressurized can that is equipped with a nozzle so that an aerosol of the formulation can be readily sprayed onto a surface. Dispensers are known in the art and are described, for example, in U.S. Pat. Nos. 4,780,100, 4,652,389, and 3,541,581 which are incorporated by reference herein. Although pressure within the dispenser, i.e., can pressure, does not appear to be critical, it may be preferred to range from about 10 to 100 psig. at 70° F. (21.1° C.).

In loading the dispenser, the non-propellant components of the aerosol formulation are mixed into a concentrate and loaded into the dispenser first. Thereafter, the liquefied gaseous propellant is inserted before the dispenser is fitted with a nozzle.

EXPERIMENTAL

In the following Table I, the preferred composition of the invention is disclosed:

TABLE I

| Ingredient | wt. % active |
|---|---|
| Buffer (NaOH) | 0.007 |
| Dispersing/emulsifying/wetting agent[1] | 0.03 |
| Fragrance[2] | 0.25 |
| Corrosion Inhibitor[3] | 0.6 |
| Quaternary Ammonium Compound[4] | 0.63 |
| Anionic Polymer[5] | 1.05 |
| Propellant[6] | 10 |
| Water | 122.433 |
| Ethanol | 65 |
| Total | 100 |

[1]Byk Chemie BYK-345
[2]Proprietary
[3]NaNO2
[4]Stepan BTC-885
[5]B. F. Goodrich GA 2123
[6]Diversified CPC Int'l A-46

The films resulting from the dispensing and curing of this formulation resulted in elegant, smooth, glassy appearing translucent films which demonstrated good water resistance. However, it is the disinfectancy and residual efficacy performance which was especially noteworthy and unexpected.

In the following experiments, it should be noted that disinfectancy (contact efficacy or kill) is assessed by a 10 minute contact on a surface containing a given titer of microorganisms, whose reduction after 10 minute contact is compared to a control. The residual efficacy studies generally are determined by repeated inoculation of a surface with a given microorganism, with rinsing or other removal of materials from the surface between the inoculations, which are adapted from standard AOAC/ASTM and other protocols.

The disinfecting (contact efficacy) tests are disclosed in Tables II–V below, in which the inventive formulation is tested against bacteria, viruses and fungi, respectively.

TABLE II

Bacterial Disinfectancy

| | | | Number of carriers |
|---|---|---|---|
| Lot Number | Organism | Exposed | Showing Growth |
| Lot #1 | Staphylococcus aureus | 60 | 1° 0<br>2° 0 |
| | Salmonella choleraesuis | 60 | 1° 0<br>2° 0 |
| | Pseudomonas aeruginosa | 60 | 1° 0<br>2° 0 |
| Lot #2 | Staphylococcus aureus | 60 | 1° 0<br>2° 0 |
| | Salmonella choleraesuis | 60 | 1° 0<br>2° 0 |
| | Pseudomonas aeruginosa | 60 | 1° 0<br>2° 0 |
| Lot #3 | Staphylococcus aureus | 60 | 1° 0<br>2° 0 |
| | Salmonella choleraesuis | 60 | 1° 0<br>2° 0 |
| | Pseudomonas aeruginosa | 60 | 1° 0<br>2° 0 |

1° = primary subculture growth; 2° = secondary subculture growth.

The inventive composition resulted in complete inactivation of each viral strain. The exemplary performance results are demonstrated below in Table III.

TABLE III

Virucidal Efficacy

| Virus | Dried Virus Control | Lot 3 Virus Exposure | Lot 4 Virus Exposure | Cytotoxicity Lot 3 | Cytotoxicity Lot 4 | Virus Reduction Titer |
|---|---|---|---|---|---|---|
| Poliovirus type 1 | $10^{6.75}$ | $\leq 10^{2.5}$ | $\leq 10^{2.5}$ | $\leq 10^{2.5}$ | $\leq 10^{2.5}$ | $\geq 4.25 \log_{10}$ Complete Inactivation |
| Influenza Virus type A2 | $10^{4.75}$ | $\leq 10^{1.5}$ | $\leq 10^{1.5}$ | $\leq 10^{1.5}$ | $\leq 10^{1.5}$ | $\geq 3.25 \log_{10}$ Complete Inactivation |
| HIV type 1 | $10^{6.5}$ | $\leq 10^{3.5}$ | $\leq 10^{3.5}$ | $\leq 10^{3.5}$ | $\leq 10^{3.5}$ | $\leq 3.0 \log_{10}$ Complete Inactivation |

TABLE IV

Anitfungal Efficacy

| Sample Lot | Organism | Tiles | Visual Evaluation of Test Tiles | Magnified Evaluation of Test Tiles |
|---|---|---|---|---|
| Lot 3 | Aspergillus niger | 1–10 | no growth (0%) | no growth (0%) |
| Lot 4 | Aspergillus niger | 1–10 | no growth (0%) | no growth (0%) |
| Untreated Control Tiles | Aspergillus niger | 1–10 | growth (75–95%) | |

TABLE V

Anitfungal Efficacy

| | | Number of Carriers | |
|---|---|---|---|
| Sample Lot | Organism | Exposed | Showing Growth |
| Lot 3 | Tricophyton metagrophytes | 10 | 1° 0<br>2° 0 |
| Lot4 | Tricophyton metagrophytes | 10 | 1° 0<br>2° 0 |

The residual efficacy results are captured below in Tables VI–XI. Tables VI and IX show the controls in which bacterial growth are observed, Tables VII and X show the residual efficacy data, and Tables VIII and XI show reduction calculations. In the data, "CFU" means "colony forming units, a standard measure in microbiology.

TABLE VI

Control Counts

| Test Organism | Carrier Designation | Zero Time Counts - CFU/Carrier | Control Counts - CFU/Carrier |
|---|---|---|---|
| Stapylococcus aureus | A | $6.4 \times 10^5$ | $1.4 \times 10^6$ |
| | B | $5.3 \times 10^5$ | $9.3 \times 10^5$ |
| | C | Avg = $5.9 \times 10^5$ | Avg. = $1.0 \times 10^6$ |
| Klebsiella pneumoniae | A | $1.4 \times 10^6$ | $1.3 \times 10^6$ |
| | B | $1.5 \times 10^6$ | $1.6 \times 10^6$ |
| | | Avg. = $1.5 \times 10^6$ | Avg. = $1.6 \times 10^6$ |
| | C | | $2.0 \times 10^6$ |

TABLE VII

Test Substance Tile Counts

| Test Sample No. | Test Organism | Carrier Code | No. of CFU/Carrier |
|---|---|---|---|
| L1-6 | Staphylococcus aureus | A | 15 |
|  |  | B | no observable colonies |
|  |  | C | 45 |
| L1-6 | Klebsiella pneumoniae | A | 690 |
|  |  | B | 135 |
|  |  | C | 660 |
| L2-1 | Staphylococcus aureus | A | 30 |
|  |  | B | 45 |
|  |  | C | 75 |
| L2-1 | Klebsiella pneumoniae | A | 195 |
|  |  | B | 195 |
|  |  | C | 135 |

TABLE VIII

% Reduction Calculations

| Test Sample No. | Test Organism | Carrier Code | % Reduction vs. Control |
|---|---|---|---|
| L 1-6 | Staphylococcus aureus | A | 99.9 |
|  |  | B | >99.9 |
|  |  | C | 99.9 |
| L 1-6 | Klebsiella pneumoniae | A | 99.9 |
|  |  | B | 99.9 |
|  |  | C | 99.9 |
| L2-1 | Staphylococcus aureus | A | 99.9 |
|  |  | B | 99.9 |
|  |  | C | 99.9 |
| L2-1 | Klebsiella pneumoniae | A | 99.9 |
|  |  | B | 99.9 |
|  |  | C | 99.9 |

TABLE IX

Control Counts

| Test Organism | Carrier Designation | Control Counts - CFU/Carrier |
|---|---|---|
| Salmonella choleraesuis | A | $2.5 \times 10^5$ |
|  | B | $1.9 \times 10^5$ |
|  | C | $4.8 \times 10^5$ |
| Escherichia coli 0157:H7 | A | $6.4 \times 10^5$ |
|  | B | $5.8 \times 10^5$ |
|  | C | $6.4 \times 10^5$ |

TABLE X

Test Substance Tile Counts

| Test Organism | Carrier Code | No. of CFU/Carrier |
|---|---|---|
| Salmonella choleraesuis | A | 315 |
|  | B | 450 |
|  | C | 195 |
| Escherichia coli 0157:117 | A | 30 |
|  | B | 30 |
|  | C | no observable colonies |

TABLE XI

% Reduction Calculations

| Test Organism | Carrier Code | % Reduction vs. Control |
|---|---|---|
| Salmonella choleraesuis | A | 99.9 |
|  | B | 99.9 |
|  | C | 99.9 |
| Escherichia coli 0157:H7 | A | 99.9 |
|  | B | 99.9 |
|  | C | >99.9 |

The foregoing data in Tables VIII and XI demonstrate generally excellent broad spectrum residual efficacy versus both gram negative and gram positive bacteria.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An aerosol antimicrobial dispensable composition comprising:
    (a) about 0.01 to 15% of an anionic polymer or prepolymer, which has an acid number greater than 10 wherein the polymer may be completely or partly neutralized by a quaternary ammonium compound, said polymer having a molecular weight range from 100 to 2,000,000 Daltons;
    (b) about 0.01 to 5% of said quaternary ammonium compound, the components (a) and (b) combining to form an antimicrobially effective complex;
    (c) at least one water-soluble or dispersible organic solvent having a vapor pressure of at least 0.001 mm Hg at 25° C. and selected from the group consisting of $C_{1-6}$ alkanols, $C_{1-6}$ diols. $C_{1-6}$ alkyl ethers of alkylene glycols and polyalkylene glycols, and mixtures thereof, said at least one organic solvent being at least 20% of the composition;
    (d) about 1% to 50% of a propellant; and
    (e) less than 70% water.

2. The composition of claim 1 wherein said anionic polymer or prepolymer is acrylate copolymer.

3. The composition of claim 1 wherein the quaternary ammonium compound is selected from the group consisting of mono-long-chain, tri-short-chain, tetraalkyl ammonium compounds, di-long-chain, di-short-chain tetraalkyl ammonium compounds, trialkyl mono-benzyl ammonium compounds, and mixtures thereof.

4. The composition of claim 3 wherein said quaternary ammonium compound is a mixture of trialkyl, mono-benzyl ammonium and di-long-chain, di-short-chain tetraalkyl ammonium compounds.

5. The composition of claim 1 wherein said organic solvent of (c) is selected from the group consisting of alkanols, diols, polyalkylene glycols, alkyl ethers of alkylene glycols and polyalkylene glycols, and mixtures thereof.

6. The composition of claim 5 wherein said organic solvent is a $C_{1-6}$ alkanol.

7. The composition of claim 1 wherein said propellant is selected from compressed or compressible gases and hydrocarbon propellants.

8. The composition of claim 1 further comprising a dispersing, wetting or emulsifying agent.

9. The composition of claim 8 wherein said dispersing, wetting or emulsifying agent is selected from anionic, nonionic, cationic, amphoteric surfactants; hydrotropes; and mixtures thereof.

10. The composition of claim 9 wherein said dispersing, wetting or emulsifying agent is a modified polysiloxane.

11. The composition of claim 1 further comprising at least one adjunct selected from the group consisting of corrosion inhibitors, chelants, buffers, fragrances, perfumes, thickeners, dyes, colorants, pigments, water-insoluble organic solvents, additional antimicrobial compounds, and mixtures thereof.

12. A method for treating a surface containing microorganisms, or which could contain said microorganisms thereafter, said method comprising the steps of:
 (i) delivering an admixture via a propellant, wherein the admixture and propellant are derived from an aerosol composition comprising:
  (a) about 0.01 to 15% of an anionic polymer or prepolymer, which has an acid number greater than 10 wherein the polymer may be completely or partly neutralized by a quaternary ammonium compound, said polymer having a molecular weight range from 100 to 2,000,000 Daltons;
  (b) about 0.01 to 5% of sad quaternary ammonium compound, the components (a) and (b) combining to form an antimicrobially effective complex;
  (c) at least one water-soluble or dispersible organic solvent having a vapor pressure of at least 0.001 mm Hg at 25° C. and selected from the group consisting of $C_{1-6}$ alkanols, $C_{1-6}$ diols, $C_{1-6}$ alkyl ethers of alkylene glycols and polyalkylene glycols, and mixtures thereof, said at least one organic solvent being at least 20% of the composition;
  (d) about 1% to 50% of a propellant; and
  (e) less than 70% water; and
 (ii) applying said admixture to a surface.

13. A device for dispensing an aerosol antimicrobial composition which comprises:
 a closed container containing said composition, said composition comprising:
  (a) about 0.01 to 15% of an anionic polymer or prepolymer, which has an acid number greater than 10 wherein the polymer may be completely or partly neutralized by a quaternary ammonium compound, said polymer having a molecular weight range from 100 to 2,000,000 Daltons;
  (b) about 0.01 to 5% of said quaternary ammonium compound, the components (a) and (b) combining to form an antimicrobially effective complex;
  (c) at least one water-soluble or dispersible organic solvent having a vapor pressure of at least 0.001 mm Hg at 25° C. and selected from the group consisting of $C_{1-6}$ alkanols, $C_{1-6}$ diols, $C_{1-6}$ alkyl ethers of alkylene glycols and polyalkylene glycols, and mixtures thereof, said at least one organic solvent being at least 20% of the composition;
  (d) about 1% to 50% of a propellant; and
  (e) less than 70% water.

14. A film or residue on a surface from the application of a dispensable antimicrobial composition to said surface, said aerosol composition comprising:
 (a) about 0.01 to 15% of an anionic polymer or prepolymer, which has an acid number greater than 10 wherein the polymer may be completely or partly neutralized by a quaternary ammonium compound, aid polymer having a molecular weight range from 100 to 2,000,000 Daltons;
 (b) about 0.01 to 5% of said quaternary ammonium compound, the components (a) and (b) combining to form an antimicrobially effective complex;
 (c) at least one water-soluble or dispersible organic solvent having a vapor pressure of at least 0.001 mm Hg at 25° C. and selected from the group consisting of $C_{1-6}$ alkanols, $C_{1-6}$ alkyl ethers of alkylene glycols and polyalkylene glycols, and mixtures thereof, said at least one organic solvent being at least 20% of the composition;
 (d) about 1% to 50% of a propellant; and
 (e) less than 70% water.

* * * * *